United States Patent [19]

Lee

[11] Patent Number: 4,607,129

[45] Date of Patent: Aug. 19, 1986

[54] CATALYTIC DEHYDROCYCLIZATION AND DEHYDROGENATION OF HYDROCARBONS

[75] Inventor: Fu M. Lee, Bartlesville, Okla.

[73] Assignee: Phillips Petroleum Company, Bartlesville, Okla.

[21] Appl. No.: 742,678

[22] Filed: Jun. 10, 1985

[51] Int. Cl.$^4$ ................................................. C07C 5/42
[52] U.S. Cl. ................................... 585/415; 585/407; 585/417; 585/661; 585/616; 585/379; 208/134
[58] Field of Search ............... 585/415, 407, 417, 661, 585/662, 663, 616, 629, 379; 208/134

[56] References Cited

U.S. PATENT DOCUMENTS

| | | | |
|---|---|---|---|
| 2,189,815 | 2/1940 | Morrell et al. | 585/661 |
| 2,570,067 | 10/1951 | Myers | 585/661 |
| 2,785,141 | 3/1957 | Fleck | 585/661 |
| 2,814,650 | 11/1957 | Clerk | 585/661 |
| 3,228,992 | 1/1966 | Myers | 585/661 |
| 4,443,640 | 4/1984 | van der Meijden et al. | 585/418 |

OTHER PUBLICATIONS

"Petroleum Refining", J. H. Gary and G. E. Handwerk; Marcel Dekker, Inc.; New York; 1975, pp. 65–69.

Primary Examiner—Andrew H. Metz
Assistant Examiner—A. Pal

[57] ABSTRACT

A process is provided for converting alkanes and cycloalkanes having up to 20 carbon atoms per molecule to a product comprising hydrogen gas and dehydrogenated and/or dehydrocyclized hydrocarbons, in the presence of a catalyst composition comprising divanadium pentoxide and silica. In one embodiment, a substantially deactivated catalyst composition is regenerated by contacting it with a free oxygen containing gas under suitable regeneration conditions. In another embodiment, a catalyst composition comprising divanadium pentoxide and silica is provided.

17 Claims, No Drawings

CATALYTIC DEHYDROCYCLIZATION AND DEHYDROGENATION OF HYDROCARBONS

BACKGROUND OF THE INVENTION

In one aspect, this invention relates to the catalytic dehydrogenation of alkanes to alkenes. In another aspect, this invention relates to the catalytic dehydrocyclization of alkanes to cycloalkenes and aromatic hydrocarbons. In still another aspect, this invention relates to the catalytic dehydrogenation of cycloalkanes to cycloalkenes and aromatic hydrocarbons. In a further aspect, this invention relates to a catalytic process for upgrading gasoline-type hydrocarbon mixtures to fuels having a higher octane rating.

Catalytic processes for the dehydrogenation and/or dehydrocyclization of alkanes and cycloalkanes are well known. Also processes for reforming of gasoline-type hydrocarbon fractions to fuels of higher octane rating are commercially practiced. However, there is an ever present need to develop new processes employing more effective catalysts for these important processes.

SUMMARY OF THE INVENTION

It is an object of this invention to provide a process for converting alkanes to alkenes and/or cycloalkenes and/or aromatic hydrocarbons by catalytic dehydrogenation and/or dehydrocyclization. It is another object of this invention to convert cycloalkanes to cycloalkenes and/or aromatic hydrocarbons by catalytic dehydrogenation. It is a further object of this invention to increase the octane number of gasoline-type hydrocarbons by reforming them in a dehydrogenation and/or dehydrocyclization reaction over a new reforming catalyst. It is a still further object to provide a process for regenerating a new reforming (dehydrogenation/dehydrocyclization) catalyst. It is still another object of this invention to provide a catalyst composition having improved dehydrogenation/dehydrocyclization activity. Other objects and advantages will be apparent from the detailed description and the appended claims.

In accordance with this invention, a hydrocarbon containing feed stream comprising at least one hydrocarbon selected form the group consisting of alkanes containing from 2 to 20 carbon atoms per molecule and cycloalkanes containing from 5 to 20 carbon atmos per molecule is contacted with a catalyst composition comprising (a) divanadium pentoxide and (b) silica, under such reaction conditions as to convert at least a portion of said hydrocarbon feed to a product comprising hydrogen gas and at least one hydrocarbon selected from the group consisting of alkenes containing from 2 to 20 carbon atoms, alkadienes containing from 4 to 20 carbon atoms per molecule, cycloalkenes containing from 5 to 20 carbon atoms per molecule, cycloalkadienes containing from 5 to 20 carbon atoms per molecule and aromatic hydrocarbons containing from 6 to 20 carbon atoms per molecule. In one embodiment, said catalyst composition is provided, which is particularly suited for use in reforming processes.

In a preferred embodiment, said hydrocarbon containing feed stream comprises at least one alkane containing from 2 to 12 carbon atoms per molecule and said product comprises at least one aromatic hydrocarbon having from 6 to 12 carbon atoms. The product contains at least one molecule $H_2$ more than the feedstream for every unsaturation created and/or for every ring formed. In another embodiment of this invention, a hydrocarbon feed mixture comprising alkanes containing from 5 to 12 carbon atoms per molecule and having a boiling range of about 50° F. to about 430° F. under standard pressure conditions (about 1 atmosphere) is contacted with a catalyst composition comprising (a) divanadium pentoxide and (b) silica, under such conditions as to increase the octane number of said hydrocarbon mixture.

In still another embodiment, a catalyst composition that comprises (a) divanadium pentoxide and (b) silica which has been contacted with a hydrocarbon feed in accordance with this invention is then regenerated by contacting said catalyst composition with a free oxygen containing gas under such conditions as to enhance the dehydrogenation and/or dehydrocyclization activity of said catalyst composition. It is presently believed that a portion of the divanadium pentoxide contained in the catalyst is reduced to one or more oxides of vanadium having a lower valence state during said contacting with the hydrocarbon feed according to the process of this invention, and that said subsequent contacting of the catalyst with a free oxygen containing gas causes reoxidation of said lower valent vanadium oxides to divanadium pentoxide.

DETAILED DESCRIPTION OF THE INVENTION

The catalyst composition of this invention comprises (a) divandium pentoxide and (b) silica. It is within the scope of this invention to have, in addition to the divandium pentoxide, other oxides of vanadium (e.g., $VO_2$, $V_2O_3$, $VO$) present in the catalyst composition. It is also within the scope of this invention, to have, in addition to divanadium pentoxide, other metal oxides or sulfides such as $MoO_3$, $NiO$, $MoS_3$, $NiS$ and the like present in the catalyst composition. It is further within the scope of this invention, to have, in addition to silica, other inorganic refractory oxides such as alumina, silica-aluminas, titania, zirconia, magnesia and aluminum phosphate present in the catalyst composition.

The catalyst composition of this invention can be prepared by any suitable method. Generally, a high surface area silica (preferably amorphous) is impregnated with a solution of a suitable vanadium compound, and the thus impregnated silica is then heated (calcined), preferably in a free oxygen containing gas, so as to convert at least a substantial portion of said vanadium compound to divanadium pentoxide. Suitable calcining conditions are 900° to 1300° F. under 0 to 20 psig pressure.

Suitable vanadium compounds that can be converted to $V_2O_5$ upon heating are vanadium nitrates, ammonium vanadates, vanadium carboxylates, vanadium acetylacetonates, vanadium alcoholates and the like. The presently preferred impregnating solution is one containing vanadium oxobis(1-phenyl-1,3-butane dionate) as the solute and toluene as the solvent. Any silica, preferably substantially amorphous silica, that has a surface area (determined by the BET/$N_2$ method; ASTM D3037) ranging from about 50 to about 500 m$^2$/g, preferably from about 200 to about 400 m$^2$/g, can be utilized. The amorphous silica can be prepared by any suitable technique such as vapor-phase hydrolysis or wet precipitation. A presently preferred, commercially available silica is described in Example I.

The $V_2O_5$ content of the catalyst composition of this invention can range from about 0.01 to about 40 weight- %, preferably from about 2 to about 10 weight-% $V_2O_5$, based on the entire catalyst composition. The surface area (determined by the BET/$N_2$ method; ASTM D3037) of the finished $V_2O_5$/$SiO_2$-containing catalyst composition of this invention ranges from about 50 to about 500 m$^2$/g, preferably from about 150 to about 300 m$^2$/g. The pore volume (determind by the BET/$N_2$ method) of the $V_2O_5$/$SiO_2$-containing catalyst composition ranges from about 0.3 to about 4 cc/g, preferably from about 0.5 to about 2 cc/g.

The hydrocarbon feed to be treated in the process of this invention can contain at least one alkane having from 2 to 20 carbon atoms per molecule. Non-limiting examples of suitable alkanes are: ethane, propane, n-butane, isobutane, 2-methylbutane, n-pentane, 2-methylpentane, n-hexane, 3-methylhexane, 2,3-dimethylhexane, n-heptane, n-octane, n-decane, 3,4-dimethyldecane, 3-ethyldecane, n-dodecane, n-hexadecane, n-octadecane, 3-ethyloctadecane and the like. Presently preferred alkanes are those containing 3–8 carbon atoms per molecule.

the hydrocarbon feed can also contain at least one cycloalkane having from 5 to 20 carbon atoms per molecule. Non-limiting examples of suitable cycloalkanes are cyclopentane, cyclohexane, cycloheptane, cyclooctane, cyclodecane, methylcyclopentane, methylcyclohexane, 1,3-dimethylcyclohexane, 1,4-dimethylcyclohexane, ethylcyclohexane, methylcyclodecane, 1,3-dimethylcyclodecane, 1,3-dimethyl-5-propylcyclodecane and the like. Presently preferred cycloalkanes are methylcyclopentane, cyclohexane, methylcyclohexane, 1,3-dimethylcyclohexane, ethylcyclohexane.

The hydrocarbon feed can also be a fraction of a petroleum crude oil, or a fraction of a catalytic cracker effluent, or a fraction of a shale oil, or a fraction of a product produced by extraction or liquefaction of coal, or of similar hydrocarbon feed stocks. Presently, a petroleum fraction boiling at atmospheric pressure in the range of about 50° F. to about 430° C. can be utilized such as a gasoline or naphtha fraction. These fractions generally contain alkanes having from 5 to 12 carbon atoms per molecule as major components.

Any apparatus which will afford an intimate contact of the hydrocarbon containing feed stream with the catalyst composition of this invention at an elevated temperature can be employed. The process is in no way limited to a particular apparatus. The process can be carried out in a batch process, e.g., in an autoclave which can be heated and pressured and preferably, contains internal agitating or circulating pumping means. The catalyst composition can be dispersed in the feed, or it can be used as a fixed bed through which the hydrocarbon containing feed flows. Or the process can be carried out as a continuous process, e.g., in a tubular reactor containing the catalyst composition as a fixed bed. The term "hydrocarbon containing feed stream" is used herein to both batch and continuous process.

The dehydrogenation/dehydrocyclization process of this invention can be carried out at any suitable temperature that is effective, yet safe for splitting off hydrogen from the feed hydrocarbons. Generally, the reaction temperature ranges from about 750° F. to about 1300° F., preferably from about 850° F. to about 1200° F., more preferably from about 900° F. to about 1100° F.

Any suitable reaction pressure can be utilized in the dehydrogenation process of this invention. The reaction pressure can range from approximately atmospheric (about 15 psia=0 psig) to as high as 100 psig. Preferably, the reaction pressure ranges from about 0 psig to about 50 psig, more preferably from about 0 psig to about 20 psig. Preferably the reaction is carried out in the absence of added hydrogen.

Any suitable reaction time, i.e., the time of intimate contact of the hydrocarbon containing feed stream with the catalyst composition at suitable reaction conditions so as to remove hydrogen from said feed hydrocarbons, can be used in the process of this invention. The actual reaction time will greatly depend on such features as the selection of an effective, yet safe reaction temperature, the type of feed used, the type of catalyst bed employed and the particle size of the catalyst. Generally, the reaction time ranges from about 1 to about 20 seconds, preferably from about 4 to about 8 seconds. In a continuous process, the reaction time is generally expressed in terms of the weight hourly space velocity (weight of feed hydrocarbon/weight catalyst/hour), which can range from about 0.1 to about 10 g feed/g catalyst/hour, preferably from about 1 to about 2 g feed hydrocarbon/g catalyst/hour for the dehydrocyclization of alkanes, and preferably from about 1 to about 5 g feed hydrocarbon/g catalyst/hour for dehydrogenation of cycloalkanes.

The dehydrogenated products formed in the process of this invention are preferably separated from the reaction mixture by any separation means such as condensation, distillation, selective adsorption or absorption, extraction and the like, more preferably by fractional distillation. When the product is a mixture of compounds, further separation into individual compounds or fractions having a specific boiling range is preferably carried out. Unconverted feed hydrocarbons are preferably recycled to the reaction zone. Hydrogen gas which is formed during the process of this invention is preferably separated from other gaseous materials in any suitable conventional manner and can be used as fuel or as a reactant for chemical syntheses or chemical treating operations that require hydrogen (e.g., catalytic hydrotreating or hydrocracking of heavy oils).

The catalyst composition of this invention gradually loses its catalytic activity by at least partial reduction of the divanadium pentoxide to oxides of vanadium having a lower valence state during the process of this invention. In one embodiment of this invention, a substantially deactivated catalyst composition is regenerated by interrupting the flow of hydrocarbon feed and contacting the catalyst composition with a free oxygen containing gas (preferably air) at such regeneration conditions as will result in the re-oxidization of the vanadium oxide to divanadium pentoxide. The term'- 'substantially deactivated catalyst composition" as used herein means a catalyst composition that has lost a sufficiently high portion of its initial activity due to the reduction of $V_2O_5$ that it no longer converts the feed hydrocarbon to the desired products at commercially acceptable yields. This regeneration process can be carried out in a separate reactor or it can be carried out in the same reactor as is used for the dehydrogenation/dehydrocyclization process except that no hydrocarbon feed stream is passed through the reactor but a free oxygen containing gas, preferably air. Typical regeneration conditions comprise a temperature ranging from about 700° F. to about 1300° F., using air as the free oxygen containing gas. Between contacts of hydrocarbon and oxygen, the catalyst composition is preferably stripped by passing a stripping fluid such as nitrogen or other inert gases (e.g., He, Ar) through the catalyst composition.

In another embodiment of this invention, a swing-reactor operation with at least two parallel reactors containing catalyst beds employed for the regeneration of the catalyst. In this type of operation, the hydrocarbon feed flows through the first reactor under dehydrogenation/dehydrocyclization conditions. After the activity of the catalyst composition of this invention in the first reactor has decreased to an unacceptable level, a series of valves are actuated so that the feed is passed through at least one other reactor containing the catalyst composition of this invention under dehydrogenation/dehydrocyclization reaction conditions, while air is passed through the first reactor under the above described regeneration conditions. When the catalyst composition in said other reactor has been subsantially deactivated, appropriate valves are actuated so as to pass the hydrocarbon containing feed through the first reactor containing the regenerated catalyst composition and to pass air through said other reactor for catalyst regeneration. This cycle can be repeated many times. Stripping as described above is also preferably employed to prevent oxygen and hydrocarbon contact and to recover more hydrocarbon products.

The following examples are presented to further illustrate this invention without unduly limiting the scope of this invention.

EXAMPLE I

In this example the preparation of supported divanadium pentoxide catalysts is described.

Invention Catalyst A ($V_2O_5$ on silica) was prepared as follows. A sample of 50 grams of silica (provided by Davison Chemical Division of W. R. Grace and Company, Baltimore, MD; surface area: 340 $m^2/g$; pore volume: 1.15 cc/g; volatile content at 1750° F.: 6.5%; bulk density: 25 lb/$ft^3$) was mixed at room temperature with a solution of 7.33 g of vanadium oxobis-(1-phenyl-1,3-butane-dionate) (provided by Eastman Kodak, Rochester, NY) in 200 mL of toluene. The mixture was slowly dried by heating in a ceramic drying dish. The dried, impregnated silica material was calcined in air for about 30 minutes at about 1200° F. under hydrogen (for reduction) and under air (for oxidation) in 10 alternating cycles each lasting about 5 minutes. The thus calcined and redox-treated $V_2O_5/SiO_2$ catalyst contained about 1.3 weight-% V, had a surface area (determined by BET/$N_2$; ASTM D3037) of 236 $m^2/g$ and a pore volume (determined by the BET/$N_2$ method) of 0.95 cc/g.

Control Catalyst B ($V_2O_5$ on alumina) was prepared by impregnating a sample of 25.2 g of alumina (surface area: 254 $m^2/g$; pore volume: 0.62 cc/g) with a solution of 2.5 g of vanadium oxobis-(1-phenyl-1,3-butane-dionate) in toluene. Drying, calcining and aging of the $V_2O_5/Al_2O_3$ catalyst was carried out essentially in accordance with the procedure described for Catalyst A. The thus calcined and redox-treated $V_2O_5/Al_2O_3$ catalyst contained about 1.2 weight-% V, had a BET/$N_2$ surface area of 153 $m^2/g$ and a pore volume (determined by the BET/$N_2$ method) of 0.56 cc/g.

Control Catalysts C and D were prepared by impregnation of a Super DX zeolite-containing cracking catalyst (provided by Davison Chemical Division of W. R. Grace and Company; surface area: 70.2 $m^2/g$; pore volume: 0.34 cc/g) that was steam aged with 100% steam at 1275° F. under 40 psig pressure for 21 hours. The impregnation of two 50 gram samples of steam-aged Super DX with solutions of 1.84 g and 7.33 g, respectively, of vanadium oxobis-(1-phenyl-1,3-butane-dionate) and the subsequent drying, calcining and redox-treatment of the vanadium impregnated catalysts were carried out essentially in accordance with the procedure described for Catalyst A. Catalyst C contained 0.44 weight-% V, had a surface area of 53.3 $m^2/g$ and a pore volume of 0.34 cc/g. Catalyst D contained 1.6 weight-% V, had a surface area of 32.7 $m^2/g$ and a pore volume of 0.29 cc/g.

EXAMPLE II

This example illustrates the conversion of n-octane to olefins and aromatics by dehydrogenation/dehydrocyclization over Catalysts A and B. The liquid feed (n-octane) was fed by means of a syringe pump through a 2 mm capillary tube into a heated vaporization chamber where the liquid was vaporized. The feed then passed through a heated catalyst bed. The feed flow rate generally ranged from about 2 to 4 WHSV (weight hourly space velocity; g feed/hour/g catalyst) and the weight ratio of catalyst to total feed used generally ranged from about 1.5 to 2. The reaction temperature was about 950° F. The liquid reaction products were collected in a trap cooled to 32° F., and non-condensed, gaseous products were collected in a gas receiver at room temperature. Liquid and gas products were analyzed by gas chromatography. Coke formation as determined from the weight gain of the catalyst after each run. Representative test results with catalysts A and B are summarized in Table I.

TABLE I

|  | Run 1 | Run 2 |
| --- | --- | --- |
| Catalyst[1] | A (Invention) | B (Control) |
| WHSV | 4.0 | 2.9 |
| Catalyst/Feed Wt. Ratio | 1.7 | 1.9 |
| % Conversion | 29.8 | 39.7 |
| Wt % of Products: |  |  |
| Methane | 0.57 | 2.42 |
| Ethane + Ethylene | 1.75 | 11.39 |
| Propane + Propylene | 1.53 | 6.63 |
| Butenes | 1.13 | 4.15 |
| Pentenes | 1.32 | 3.38 |
| Hexenes | 1.25 | 3.49 |
| Heptenes | 0.33 | 1.24 |
| Octenes | 2.87 | 0.22 |
| Nonenes | 0.61 | 0.12 |
| $C_4$—$C_8$ Alkanes | 0.50 | 1.11 |
| Benzene | 0.38 | — |
| Toluene | 0.61 | 0.25 |
| Ethylbenzene | 5.13 | 0.30 |
| p-Xylene | 0.41 | 0.11 |
| m-Xylene | 0.85 | 0.21 |
| o-Xylene | 6.87 | 0.41 |
| Coke | 1.87 | 1.20 |
| $H_2$ (SCF/Barrel Feed) | 513 | 108 |
| % Yield of Aromatics | 14.25 | 1.28 |
| % Selevtivity to Aromatics[2] | 47.8 | 3.2 |

[1]Both catalysts were oxidized at 1250° F. for 30 minutes before use.
[2](% Yield of Aromatics ÷ % Conversion) × 100.

Data in Table I clearly show that the conversion of n-octane to aromatics was significantly higher for invention Catalyst A ($V_2O_5/SiO_2$) was employed than for control Catalyst B ($V_2O_5/Al_2O_3$). The lower conversion of n-octane on Catalyst A (versus Catalyst B) was probably caused by the higher feed rate employed in run 1 (with Catalyst A).

EXAMPLE III

This example illustrates the detrimental effect of hydrogen on both catalysts A and B. Both catalysts were treated with hydrogen for 20 minutes at 1250° F. before n-octane was introduced into the reactor. The reaction temperature was about 950° F. The experimental setup was the same as the one described in Example II. Test results are summarized in Table II.

TABLE II

| | Run 3 | Run 4 |
|---|---|---|
| Catalyst[1] | A | B |
| | (Invention) | (Control) |
| WSHV | 4.1 | 2.8 |
| Catalyst/Feed Wt. Ratio | 1.7 | 1.9 |
| % Conversion | 15.2 | 30.9 |
| Wt % of Products: | | |
| Methane | 0.28 | 1.81 |
| Ethane + Ethylene | 1.19 | 9.28 |
| Propane + Propylene | 0.89 | 5.45 |
| Butenes | 0.94 | 3.58 |
| Pentenes | 0.78 | 3.27 |
| Hexenes | 0.64 | 2.80 |
| Heptenes | 0.34 | 1.18 |
| Octenes | 1.97 | 0.18 |
| Nonenes | 0.37 | 0.15 |
| $C_4$–$C_8$ Alkanes | 0.15 | — |
| Benzene | 0.11 | — |
| Toluene | 0.22 | 0.13 |
| Ethylbenzene | 1.18 | 0.11 |
| p-Xylene | 0.14 | 0.06 |
| m-Xylene | 0.26 | 0.12 |
| o-Xylene | 1.58 | 0.12 |
| Coke | 0.37 | 0.35 |
| $H_2$ (SCF/Barrel Feed) | 172 | 67 |
| % Yield of Aromatics | 3.49 | 0.54 |
| % Selectivity to Aromatics | 23.0 | 1.7 |

[1] Both catalysts were pretreated with $H_2$ as described above.

Data in Table II also show that the dehydrocyclization of n-octane over invention Catalyst A produces more aromatics than the same reaction with control Catalyst B. A comparison of data in Tables I and II indicates that the reducing pretreatment of both catalysts with $H_2$ had a detrimental effect on conversion and aromatics yield. However, the detrimental effect of hydrogen on Catayst A was greater conversion decreased from 29.8% to 15.2%; aromatics yield decreased from 14.3% to 3.5%) than on Catalyst B (conversion decreased from 39.7% to 30.9%; aromatics yeild decreased from 1.28% to 0.54%).

These data indicate the desirability of the periodic regeneration of Catalyst A by heating in an oxidizing gas since hydrogen is formed during the dehydrogenation/dehydrocyclization of n-octane, and the thus generated hydrogen will gradually deactivate invention Catalyst A. This effect is confirmed by test data summarized in Table III. In Runs 6 and 7, Catalyst A was pretreated with the feed, n-octane. The dehydrogenation/dehydrocyclization conditions were the same as described in Example II.

TABLE III

| | Run 5 | Run 6 | Run 7 |
|---|---|---|---|
| Catalyst | A | A | A |
| Catalyst Pretreatment with n-Octane | None | 20 min.; 1250° F. | 40 min.; 950° F. |
| WHSV | 4.0 | 3.6 | 4.2 |
| Cat./Feed Wt-Ratio | 1.7 | 2.1 | 1.7 |
| % Conversion | 30.4 | 16.2 | 12.0 |
| Wt % of Products: | | | |
| Methane | 0.50 | 0.51 | 0.35 |
| Ethane + Ethylene | 1.64 | 2.51 | 1.70 |
| Propane + Propylene | 1.30 | 1.62 | 1.13 |
| Butenes | 1.18 | 1.11 | 0.93 |
| Pentenes | 1.19 | 1.32 | 0.97 |
| Hexenes | 0.90 | 1.32 | 0.89 |
| Heptenes | 0.44 | 0.46 | 0.32 |
| Octenes | 2.82 | 2.02 | 1.01 |
| Nonenes | 0.53 | 0.28 | 0.39 |
| $C_4$–$C_8$ Alkanes | 0.39 | 1.07 | 0.57 |
| Benzene | 0.30 | 0.05 | 0.16 |
| Toluene | 0.50 | 0.15 | 0.28 |
| Ethylbenzene | 4.52 | 0.69 | 2.32 |
| p-Xylene | 0.31 | 0.07 | 0.14 |
| m-Xylene | 0.65 | 0.15 | 0.29 |
| o-Xylene | 5.92 | 0.88 | 3.04 |
| Coke | 2.71 | 2.26 | 1.41 |
| $H_2$ (SCF/Barrel) | 440 | 106 | 265 |
| % Yield of Aromatics | 12.2 | 1.99 | 6.23 |
| % Selectivity to Aromatics | 40.1 | 12.3 | 51.9 |

EXAMPLE IV

This example illustrates the dehydrogenation/dehydrocyclization of mixed $C_6$ alkanes and cycloalkanes at 950° F. essentially in accordance with the procedure described in Example II. The hydrocarbon feed composition was as follows: 95.4 weight-% n-hexane, 2.2 weight-% methylcyclopentane, 1.5 weight-% 3-methylpentane, 0.7 weight-% 2-methylpentane. Three catalysts employed an invention catalyst (Catalyst $A^1$) similar to Catalyst A with 1.5 weight-% V as ($V_2O_5$) on silica, control Catalyst C (0.44 weight-% on Super DX) and control Catalyst D (1.6 weight-% V on Super DX). Test results are summarized in Table IV.

TABLE IV

| | Run 8 | Run 9 | Run 10 |
|---|---|---|---|
| Catalyst | $A^1$ | C | D |
| | (Invention) | (Control) | (Control) |
| WHSV | 4.2 | 3.3 | 3.3 |
| Cat./Feed Wt-Ratio | 1.4 | 1.8 | 1.8 |
| % Conversion | 11.8 | 15.5 | 11.2 |
| Wt % of Products: | | | |
| Methane | 0.42 | 0.96 | 0.93 |
| Ethane + Ethylene | 1.12 | 2.89 | 3.60 |
| Propane + Propylene | 1.22 | 3.48 | 3.68 |
| Butenes | 0.87 | 1.61 | 2.02 |
| Pentenes | 0.51 | 0.76 | 0.85 |
| Hexenes | 0.49 | 0.13 | 0.21 |
| Heptenes | 0.76 | — | — |
| $C_4$–$C_8$ Alkanes | — | 0.47 | 0.79 |
| Benzene | 3.01 | 0.12 | 0.14 |
| Other Aromatics | — | 0.41 | 0.43 |
| Coke | 0.50 | 0.34 | 0.68 |
| $H_2$ (SCF/Barrel) | 219 | 42 | 27 |
| % Yield of Aromatics | 3.01 | 0.53 | 0.57 |
| % Selectivity to Aromatics | 25.5 | 3.4 | 5.1 |

Data in Table IV clearly show that the production of desirable aromatics is much higher when the invention catalyst ($V_2O_5/SiO_2$) was used rather than the two control catalysts ($V_2O_5$ on a zeolite-containing cracking catalyst).

EXAMPLE V

This example illustrates the dehydrogenation of propane and isobutane over invention catalyst $A^1$, substantially in accordance with the procedure described in Example II. Test results of representative runs are summarized in Tables V and VI.

TABLE V

| | Run 11 (Invention) | Run 12 (Invention) | Run 13 (Invention) |
|---|---|---|---|
| Catalyst | A[1] | A[1] | A[1] |
| Feed | Propane | Propane | Propane |
| WHSV | 0.34 | 0.34 | 0.34 |
| Temperature (°F.) | 1000 | 1000 | 1000 |
| Run Time (minutes) | 34 | 62 | 163 |
| % Conversion | 51.5 | 49.4 | 48.4 |
| Wt % of Products: | | | |
| Methane | 4.43 | 5.54 | 6.50 |
| Ethane | 4.64 | 5.52 | 5.06 |
| Ethylene | 2.73 | 3.26 | 3.57 |
| Propylene | 30.36 | 29.77 | 26.69 |
| Isobutane | 3.61 | 0.25 | 0.20 |
| n-Butane | 0.24 | 0.20 | 0.20 |
| Butenes | 1.83 | 1.09 | 1.22 |
| $C_6$ + Hydrocarbons | 1.21 | 1.47 | 1.72 |
| % Yield of Olefins | 34.92 | 34.12 | 31.48 |
| % Selectivity to Olefins | 67.8 | 69.1 | 65.0 |
| % Selectivity to Propylene | 59.0 | 60.3 | 55.1 |

TABLE VI

| | Run 14 (Invention) | Run 15 (Invention) | Run 16 (Invention) |
|---|---|---|---|
| Catalyst | A[1] | A[1] | A[1] |
| Feed | Isobutane | Isobutane | Isobutane |
| WHSV | 0.90 | 0.90 | 0.90 |
| Temperature (°F.) | 1050 | 1050 | 1050 |
| Run Time (minutes) | 4 | 13 | 22 |
| % Conversion | 81.9 | 81.7 | 83.9 |
| Wt % of Products: | | | |
| Methane | 10.59 | 10.09 | 16.03 |
| Ethane | 3.95 | 5.91 | 6.61 |
| Ethylene | 2.93 | 4.38 | 4.94 |
| Propane | 3.99 | 4.22 | 4.24 |
| Propylene | 12.14 | 13.79 | 14.50 |
| Butanes | 4.16 | 3.33 | 2.89 |
| Isobutane | 24.57 | 17.98 | 16.38 |
| Other Butenes | 10.45 | 8.30 | 7.68 |
| $C_5$ Hydrocarbons | 2.88 | 2.62 | 2.58 |
| $C_6$ + Hydrocarbons | 2.72 | 3.27 | 3.69 |
| $CO_2$ | 0.35 | 0 | 0 |
| $H_2$ | 3.55 | 3.80 | 3.87 |
| % Selectivity to $C_4$ Olefins | 42.6 | 32.2 | 29.2 |
| % Selectivity to Isobutene | 30.0 | 22.0 | 20.1 |

Data in Tables V and VI show that propane and isobutane were dehydrogenated on a $V_2O_5$/silica catalyst to primarily propylene and isobutylene, respectively. Longer run times caused a decrease in yield of and selectivity to these olefins, apparently due to some deactivation of the catalyst as was described in Example III.

EXAMPLE VI

This example illustrates the dehydrogenation of cyclohexane over invention Catalyst A at 950° F., substantially in accordance with the experimental procedure described in Example II. Test results of three representative runs are summarized in Table VII.

TABLE VII

| | Run 17 | Run 18 | Run 19 |
|---|---|---|---|
| Catalyst | A | A | A |
| Pretreatment with $H_2$ | No | No | Yes |
| WHSV | 3.8 | 1.1 | 1.1 |
| % Conversion | 20.2 | 30.4 | 18.2 |
| Wt % of Products: | | | |
| Methane + Ethane | 0.12 | 0.13 | 0.11 |
| $C_3$—$C_6$ Olefins | 0.12 | 0.45 | 0.16 |
| $C_5$—$C_6$ Alkanes and Cycloalkanes | 0.36 | 0.58 | 0.40 |
| Cyclohexene | 1.97 | 2.39 | 1.63 |
| 1,3-Cyclohexadiene | 0.24 | 0.38 | 0.20 |
| Benzene | 16.17 | 24.27 | 11.08 |
| Hydrogen | 1.08 | 1.79 | 0.92 |
| Coke | 1.27 | 1.77 | 0.54 |
| % Selectivity of Benzene | 80.0 | 79.8 | 60.9 |

[1]Pretreatment with hydrogen gas was carried out at 1250° F. for 20 minutes.

Data in Table VII show that cyclohexane was dehydrogenated to benzene at a high selectivity. Pretreatment of the $V_2O_5$/$SiO_2$ catalyst with hydrogen caused a decrease in conversion, benzene yield and selectivity to benzene. This observation is in line with those reported in Example II (Table III).

EXAMPLE VII

This example illustrates the dehydrogenative reforming of a gasoline fraction over a $V_2O_5$/silica catalyst (containing 2 weight-% V) at a weight hourly space velocity of 1.7, a reaction temperature of 950° F. and a catalyst/oil weight ratio of 4.3:1, substantially in accordance with the experimental procedure described in Example II. The gasoline feed had the following characteristics: RON-clear octane number (ASTM) D2699): 36.2; API[60] gravity: 61.8; Reid vapor pressure: 7.5; paraffin content: 69.3 volume-%; naphthene content: 21.5 volume-%; aromatics content: 9.2 volume-%.

The dehydrogenative reforming of the gasoline as described above yielded a gasoline fraction having a RON-clear octane number of 76.1 (an increase of 40 units!) at a yield of 86.5 weight-%. In addition, about 7.4 weight-% of light gases ($C_1$–$C_4$ paraffins and olefins), 6.2 weight-% of coke and 850 SCF of hydrogen per barrel of converted feed were formed. These results demonstrate that the catalyst composition of this invention can be successfully employed for increasing the octane number of gasoline and similar hydrocarbon fuels.

Reasonable variations and modifications are possible within the scope of the disclosure and appended claims.

I claim:

1. A process comprising the step of contacting a hydrocarbon containing feed stream consisting essentially of at least one hydrocarbon selected from the group consisting of alkanes containing from 2 to 20 carbon atoms per molecule and cycloalkanes containing from 5 to 20 carbon atoms per molecule with a catalyst composition consisting essentially of (a) divanadium pentoxide and (b) silica, under such reaction conditions as to convert at least a portion of said hydrocarbon feed to a reaction product comprising hydrogen gas and at least one hydrocarbon selected from the group consisting of alkenes containing from 2 to 20 carbon atoms, alkadiene containing from 4 to 20 carbon atoms, cycloalkenes containing from 5 to 20 carbon atoms, cycloalkadienes containing from 5 to 20 carbon atoms and aromatic hydrocarbons containing from 6 to 20 carbon atoms per molecule.

2. A process in accordance with claim 1, wherein said hydrocarbon containing feed stream comprises at least one alkane containing from 2 to 12 carbon atoms per molecule and said product comprises at least one aromatic hydrocarbon containing from 6 to 12 carbon atoms.

3. A process in accordance with claim 1, wherein the content of said divanadium pentoxide in said catalyst composition ranges from about 0.01 to about 20 weight-%, based on the entire catalyst composition, and the surface area of the catalyst composition ranges from about 50 to about 500 m²/g.

4. A process in accordance with claim 1, wherein the content of said divanadium pentoxide in said catalyst composition ranges from about 2 to about 10 weight-%, based on the entire catalyst composition, and the surface area of the catalyst composition ranges from about 150 to about 300 m²g.

5. A process in accordance with claim 1, wherein said reaction conditions comprise a reaction temperature ranging from about 750° F. to about 1300° F.

6. A process in accordance with claim 2, wherein said reaction conditions comprise a reaction temperature ranging from about 850° F. to about 1200° F. and a reaction pressure ranging from about 0 psig to about 100 psig.

7. A process in accordance with claim 2, wherein said reaction conditions comprise a reaction temperature ranging from about 900° F. to about 1100° F., a reaction pressure ranging from about 0 psig to about 50 psig and a reaction time ranging from about 1 second to about 20 seconds.

8. A process in accordance with claim 1 comprising the additional step of separating said hydrocarbon reaction product from the reaction mixture.

9. A process in accordance with claim 1 comprising the additional step of separating hydrogen gas from the reaction mixture.

10. A process in accordance with claim 1, wherein unconverted feed hydrocarbons are recycled to the reaction zone.

11. A process in accordance with claim 1, wherein said feed hydrocarbon is selected from the group consisting of propane, isobutane, n-hexane, n-octane and cyclohexane.

12. A process in accordance with claim 1, wherein said feed hydrocarbon comprises a mixture of alkanes containing from 5 to 12 carbon atoms per molecule and having a boiling range of about 50° F. to about 430° F. under standard pressure conditions.

13. A process in accordance with claim 5 wherein a fixed bed containing said catalyst composition is used and said reaction conditions comprise a liquid hourly space velocity ranging from about 0.1 to about 20 g feed hydrocarbon/g catalyst/hour.

14. A process in accordance with claim 1 comprising the additional steps of interrupting the flow of said hydrocarbon feed stream after said catalyst composition has been substantially deactivated due to at least partial reduction of the divanadium pentoxide to oxides of vanadium having a lower valence state, and contacting said substantially deactivated catalyst composition with a free oxygen containing gas under such regeneration conditions as will result in the re-oxidation of said oxides of vanadium to divanadium pentoxide.

15. A process in accordance with claim 14 wherein said regeneration conditions comprise a temperature ranging from about 700° F. to about 1300° F. and the use of air as the free oxygen containing gas.

16. A process comprising the steps of
(A) adding to a first reactor and at least one other reactor being installed in parallel with said first reactor a catalyst composition consisting essentially of (a) divanadium pentoxide and (b) silica;
(B) passing a hydrocarbon containing feed stream consisting essentially of at least one hydrocarbon selected from the group consisting of alkanes containing from 2 to 20 carbon atoms per molecule and cycloalkanes containing from 5 to 20 carbon atoms per molecule with said catalyst composition in said first reactor under such reaction conditions as to convert at least a portion of said hydrocarbon feed to a reaction product comprising hydrogen gas and at least one hydrocarbon selected from the group consisting of alkenes containing from 2 to 20 carbon atoms, alkadienes containing from 4 to 20 carbon atoms, cycloalkenes containing from 5 to 20 carbon atoms, cycloalkadienes containing from 5 to 20 carbon atoms and aromatic catalysts containing from 6 to 20 carbon atoms per molecule, until said catalyst composition is substantially deactivated;
(C) interrupting the flow of said hydrocarbon containing feed stream through said first reactor and passing said feed stream through said other reactor under such conditions as are employed in step (B);
(D) passing a free oxygen containing gas through the substantially deactivated catalyst composition in said first reactor under such conditions as will result in an increase of the activity of said catalyst composition;
(E) interrupting the flow of the hydrocarbon containing feed stream through said other reactor and passing said feed through said first reactor under conditions as described in step (B); and
(F) passing a free oxygen containing gas through the substantially deactivated catalyst composition in said other reactor under such conditions as will result in an increase of the activity of said catalyst composition.

17. A process in accordance with claim 16, wherein a stripping fluid is passed through said substantially deactivated catalyst composition before said passing through of a free oxygen containing gas in steps (D) and (F).

* * * * *

UNITED STATES PATENT AND TRADEMARK OFFICE
CERTIFICATE OF CORRECTION

PATENT NO.   :   4,607,129

DATED        :   August 19, 1986

INVENTOR(S)  :   Fu Ming Lee

It is certified that error appears in the above-identified patent and that said Letters Patent is hereby corrected as shown below:

Claim 16, column 12, line 27, delete "catalysts" and insert therefor --- hydrocarbons ---.

Signed and Sealed this

Twenty-eighth Day of October, 1986

[SEAL]

Attest:

DONALD J. QUIGG

*Attesting Officer*     *Commissioner of Patents and Trademarks*

UNITED STATES PATENT AND TRADEMARK OFFICE
CERTIFICATE OF CORRECTION

PATENT NO. : 4,607,129

DATED : August 19, 1986

INVENTOR(S) : Fu Ming Lee

It is certified that error appears in the above-identified patent and that said Letters Patent is hereby corrected as shown below:

Inventor's name below the title should read:

-- [75] Inventor: Fu Ming Lee, Bartlesville, Okla.--.

Signed and Sealed this
Eleventh Day of November, 1986

*Attest:*

DONALD J. QUIGG

*Attesting Officer*        *Commissioner of Patents and Trademarks*